June 20, 1972 W. H. JESSEL, JR., ET AL Plant Pat. 3,213
CHRYSANTHEMUM PLANT
Filed Oct. 12, 1970
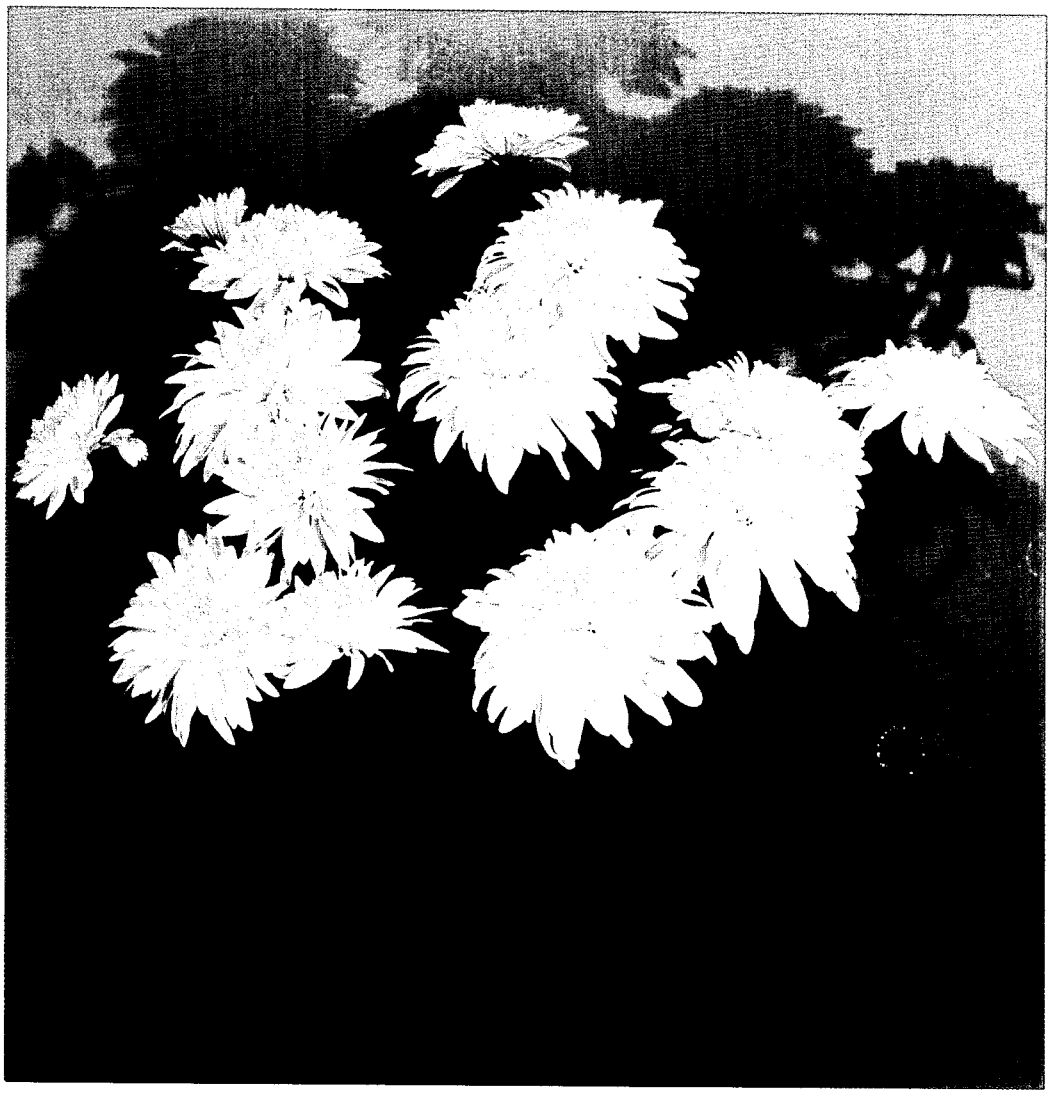
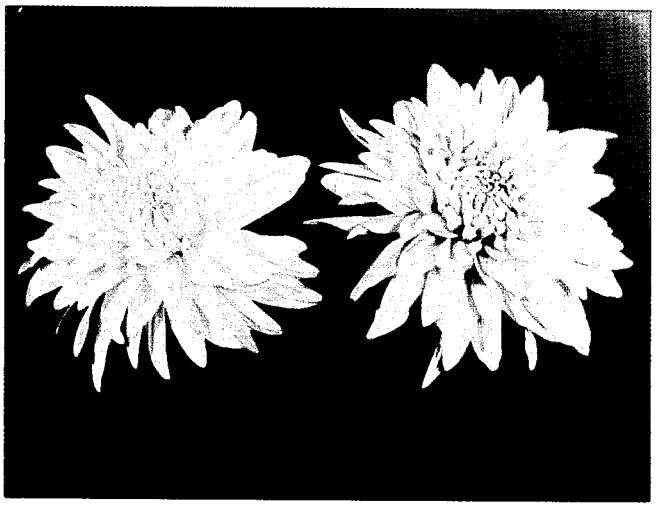
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,213
Patented June 20, 1972

3,213
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 12, 1970, Ser. No. 80,258
Int. Cl. A01h *5/00*
U.S. Cl. Plt.—78 1 Claim

The present invention comprises a new and distinct cultivar of chrysanthemum plant which is a sport of the cultivar known in the United States as Sunstar.

The new cultivar is similar in many respects to Sunstar, an unpatented but commercial cultivar of Yoder Brothers, Inc., Barberton, Ohio, the assignee of the present invention, having the same characteristics as Sunstar of:

(1) Plant habit (spread and height).
(2) Response.
(3) Flower size.
(4) Flower form.
(5) Foliage size.
(6) Foliage color.
(7) Foliage shape.

The new cultivar is distinguished from Sunstar by the following characteristics:

(1) A clear yellow color with no bronze tinging when exposed to cool temperatures in the range of 52°–58°, as is the case with Sunstar.

(2) A lighter shade of yellow.

The new cultivar was selected from a flowering block of the parent cultivar in Carpinteria, Calif., and has been asexually reproduced by cuttings at Barberton, Ohio. The new cultivar has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States and coastal California is from mid-April through October. In Florida, from December through April; and in the southern United States, the year round.

The accompanying drawing shows the unique characteristics of the new cultivar, the color being as nearly true as possible with color illustrations of this type. The upper photo shows the new cultivar by itself, and the comparison photo below shows Goldstar on the left and the parent cultivar Sunstar on the right, with both varieties being finished at cool temperatures.

In the following description, color references are made to the Munsell Color Book, 1963 edition, and comparisons have been made in certain instances with the parent cultivar Sunstar.

Botanical classification: *Chrysanthemum morifolium*

Bloom:

*Size.*—4¼″.
*Fully expanded.*—4¾″.

*Borne.*—Singly on disbudded branches.
*Stems.*—Strong.
*Form.*—Decorative.
*Permanence.*—10–14 days.

| | Goldstar | Sunstar |
|---|---|---|
| Color: | | |
| Center of flower | Yellow, 5Y8.5/12 | Golden yellow, 5Y8.5/14. |
| Base of petals | Yellow, 7.5Y8.5/10 | Light bronze, 2.5Y7/10 to yellow, 5Y8.5/12. |
| Inside of petals | do | Do. |
| Reverse of petals. | Light yellow, 7.5Y8.5/8. | Light yellow, 7.5Y8.5/8. |
| Tonality from a distance. | Yellow | Yellow or yellow streaked with light bronze, depending on finishing temperature. |
| Discoloration | do | Light bronze. |

Petals:

*Texture.*—Smooth.
*Appearance and form.*—Open at base, shallow keel, ridged tapering to a point.
*Arrangement.*—Composite, whorled on a single receptacle.
*Persistence.*—Resist shatter.
*Fragrance.*—Typical chrysanthemum.

Reproductive organs:

*Stamen, anthers.*—None to 20.
*Pollen.*—None to very scant.
*Arrangement.*—Clustered in center of flower, if present.
*Styles.*—Present both ray and disc florets.
*Length.*—Short.
*Ovaries.*—At the base of petal attached to receptacle.

Plant:

*Form.*—Herbaceous.
*Growth.*—Spreading.
*Height.*—10″–12″.
*Spread.*—6″–8″ from a single pinched plant.

Foliage:

*Top side.*—Dark green, 7.5GY2/4.
*Size.*—5″ x 3½″.
*Quantity.*—Numerious.
*Shape.*—Spatulate lobed.
*Texture.*—Smooth.
*Ribs and veins.*—Prominent.
*Edge.*—Deeply indented.
*Serration.*—Slight.
*Underside.*—Light green, 7.5GY5/4.
*Stipules.*—Small, not too conspicuous.

We claim:

1. A new and distinct cultivar of chrysanthemum characterized particularly in uniqueness when compared to the parent cultivar Sunstar by its clear, light shade of yellow color, with no bronze tinging when exposed to cool temperatures in the range of 52°–58°.

No references cited.

R. E. BAGWILL, Primary Examiner

UNITED STATES PATENT OFFICE

Certificate

Plant Patent No. 3,213 Patented June 20, 1972

Walter H. Jessel, Jr. and William E. Duffett

Application having been made by Walter H. Jessel, Jr. and William E. Buffett, the inventors named in the patent above identified, and Sandyland Nursery, Co., Carpinteria, California, the assignee, for the issuance of a certificate under the provisions of Title 35, Section 256, of the United States Code, adding the name of Mary G. Roche as a joint inventor, and a showing and proof of facts satisfying the requirements of the said section having been submitted, it is this 19th day of November 1974, certified that the name of the said Mary G. Roche is hereby added to the said patent as a joint inventor with the said Walter H. Jessel, Jr. and William E. Duffett.

FRED W. SHERLING
*Associate Solicitor.*